United States Patent [19]
Millet

[11] Patent Number: 6,146,814
[45] Date of Patent: Nov. 14, 2000

[54] METHODS OF MAKING COMPOSITE CATHETERS

[76] Inventor: Marcus J. Millet, 761 Norgate, Westfield, N.J. 07090

[21] Appl. No.: 08/997,177

[22] Filed: Dec. 24, 1997

Related U.S. Application Data

[60] Provisional application No. 60/034,038, Dec. 27, 1996.

[51] Int. Cl.$^7$ .................................................. A61M 25/16
[52] U.S. Cl. .......................... 430/320; 430/315; 430/318; 216/8
[58] Field of Search ..................... 430/315, 318, 430/319, 320; 216/8; 205/164, 165, 166, 167; 604/282

[56] References Cited

U.S. PATENT DOCUMENTS

| | | | |
|---|---|---|---|
| 5,222,949 | 6/1993 | Kaldany | 604/282 |
| 5,351,691 | 10/1994 | Brommersma | 128/662.06 |
| 5,404,638 | 4/1995 | Imran | 29/884 |
| 5,741,429 | 4/1998 | Donadio, III et al. | 216/8 |

FOREIGN PATENT DOCUMENTS

| | | |
|---|---|---|
| 6-346244 | 12/1994 | Japan . |
| WO 93/12718 | 7/1993 | WIPO . |
| WO 95/09562 | 4/1995 | WIPO . |
| WO 9602847A1 | 2/1996 | WIPO . |

OTHER PUBLICATIONS

*An Engineer's Guide to Flexible Circuit Texhnology*, Joseph Fjelstad, 1997, pp.3–13, 98–124, 188–191.

*Primary Examiner*—John A. McPherson
*Attorney, Agent, or Firm*—Lerner, David, Littenberg, Krumholz & Mentlik, LLP

[57] ABSTRACT

A polymeric tube for a medical catheter is provided with elongated metal stripes extending lengthwise along the tube by illuminating the exterior surface of the tube patternwise and treating metal responsive to the illumination. The tube may be covered with a photoresist and moved axially past a plurality of light beams while rotating the tube about its axis so as to form a helical pattern. After development of the photoresist, the metal is deposited or removed in a pattern corresponding to the pattern formed in the photoresist, so as to leave helical metallic stripes. The metallic stripes may have varying helical pitch, varying width or both along the length of the tube, and may serve as electrical connectors and physical reinforcements for the tube wall.

12 Claims, 2 Drawing Sheets

METHODS OF MAKING COMPOSITE CATHETERS

CROSS-REFERENCE TO RELATED APPLICATIONS

The present application claims benefit of United States Provisional Patent Applicaton 60/034038 filed Dec. 27, 1996, the disclosure of which is hereby incorporated by reference herein.

BACKGROUND OF THE INVENTION

A medical catheter typically has an elongated tubular polymeric body with a proximal end, which typically remains outside of the body in use, and a distal end, which is advanced into the body of the patient in use. In some cases, it is desirable to provide medical catheters with metallic elements extending lengthwise along the body of the catheter. For example, where an electrical device such as a transducer or a device for treating the body is provided at the distal end of the catheter, metallic electrical conductors may be provided to connect the electrical device to an electrical circuit at the proximal end. Alternatively or additionally, metallic elements may be provided to reinforce the physical structure of the polymeric body. The size, shape and distribution of metallic elements can substantially affect properties of the catheter such as the ease with which the tube can be bent and resistance of the tube to kinking and collapse during use.

DETAILED DESCRIPTION OF THE PREFERRED EMBODIMENTS

Figure 1:
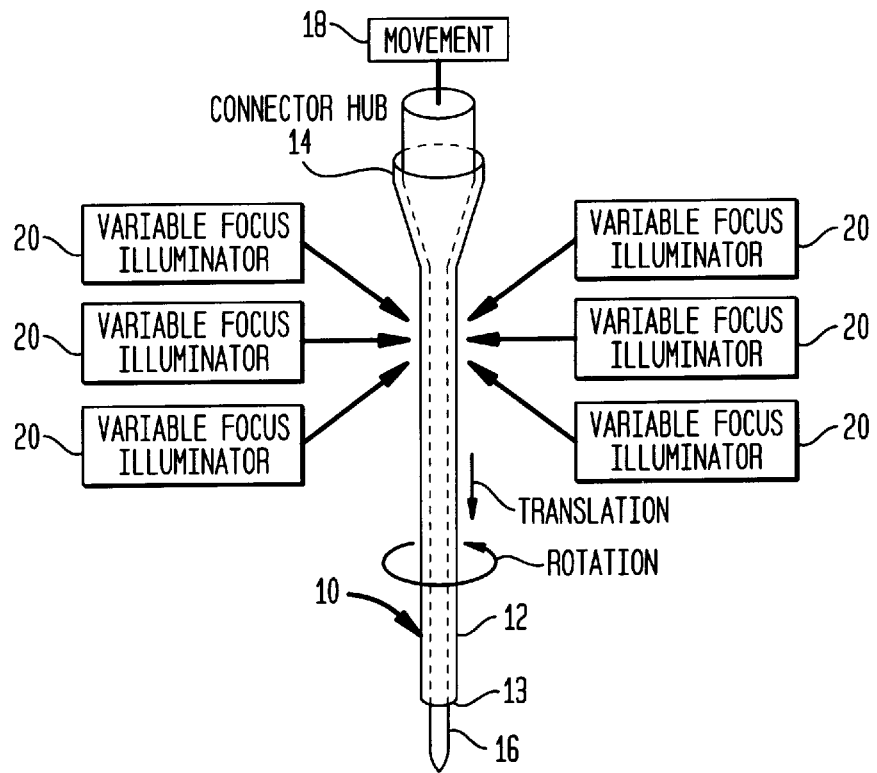
FIG. 1 is a diagrammatic view depicting a process according to one embodiment of the invention.

The present invention provides improved methods of making catheter structures. In one embodiment, a catheter 10 having a polymeric body with small-diameter tubular section 12 forming the distal end 13 of the catheter and a larger connecting section or "hub" 14 at the proximal end is provided with a layer of an etchable metal such as copper or a copper-based alloy covering the exterior surface of the catheter. For example, the exterior surface may be electrolessly plated or sputtered with a conductive metal and then electroplated to the desired thickness. Following formation of the metal layer, a layer of a photoresist is applied. The photoresist may be a conventional type as commonly used in formation of electrical circuits (commonly referred to as "printed" circuits or "flex" circuits) in the electronics industry. Following application of the photoresist, the catheter is exposed to light as shown in FIG. 1. With the catheter body supported on a mandrel 16, and the mandrel held by a movement device 18, the catheter is advanced past a bank of variable-focus illuminators 20 arranged to project beams of light radially inwardly towards a central axis. The movement device 18 simultaneously rotates and translates the mandrel which moving the catheter along the central axis. As each point on the catheter passes axially past each beam, the beam traces a helical pattern along the catheter, and exposes the photoresist in that helical pattern. After exposure to the light, the photoresist is developed, and becomes solid in the exposed regions. The unexposed photoresist is removed, leaving the metal layer covered only in the areas exposed to light. The catheter is then exposed to an etchant to remove the metal in the unexposed areas, thereby forming helical metal stripes 22 (FIG. 2) extending along the length of the catheter.

Figure 2:
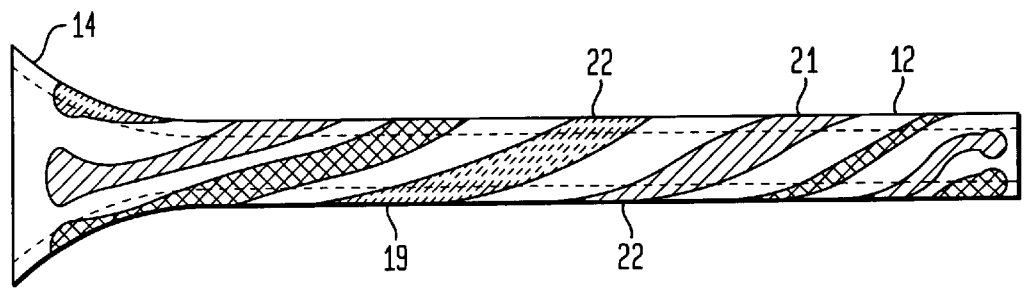
FIG. 2 is a diagrammatic elevational view depicting a catheter made in the process of FIG. 1, after completion of some manufacturing steps.

The illuminators can be actuated to vary the widths of the light beams at their point of impingement on the catheter. For example, each illuminator may include a variable-focus lens linked to a stepper motor or other electronically controllable actuator. This action is coordinated with the rotation and translation of the catheter, so as to form variable-width stripes, with wide regions 19 and narrow regions 21 at different points along the length of the catheter. One example of such a pattern is illustrated in FIG. 2, wherein each stripe 22 bears a different cross-hatching for ease of identification. Gaps 24 are provided between the stripes, as also shown on FIG. 2. Additionally, the ratio of rotational movement to translational movement can be varied during the advance of the catheter so as to vary the pitch of the helical stripes along the length of the catheter. For example, the movement device may include a stepper motor or other electronically controllable rotary actuator for turning the mandrel, and may also include an electronically controllable actuator for the translational movement. The movement device and the variable-focus illuminators may all be controlled and coordinated by a common computer (not shown) using conventional control interfaces.

The rotational movement can be entirely stopped during some part or all of the translational movement, to form straight stripes or stripes having straight portions integral with helical portions. The rotational movement can also be reversed along the length of the catheter, to form stripes with opposite pitch over different parts of the catheter length. Further one or more of the illuminators can be selectively turned off during the movement, to interrupt one or more of the stripes.

Figure 3:
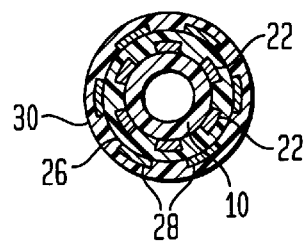
FIG. 3 is a cross-sectional view of the catheter shown in FIG. 2 at a later stage of the process.

Following formation of a first set of stripes 22, the catheter body or first polymeric layer 10 can be covered with a second polymeric layer 26 (FIG. 3) and the foregoing steps can be repeated, so as to form second metallic stripes 28 on the outside of the second polymeric layer. A further coating can then be applied over the outside of the catheter to provide a smooth surface. The coating steps can be performed by applying a curable material (e.g., an epoxy composition or, preferably, a curable polyamic acid composition which can be cured to form a polyimide), by applying a plastisol (dispersion of polymer); by applying a polymer in solution; by applying a polymer in molten form; or by any other process capable of applying a polymer layer. More than two sets of stripes can be provided, using additional polymer layers between successive sets.

Each layer of stripes can include any number of stripes, in any desired size and configuration. The ability to vary the width and helical pitch of the stripes along the length of the catheter can be used to provide different properties along the length of the catheter. For example, where a relatively flexible zone is desired, the stripes may be relatively thin; where a stiff region is desired, the stripes may be relatively wide. In a particularly preferred arrangement, the different sets of stripes in different layers (such as the first stripes 22 and second stripes 28 in FIG. 3) have opposite pitches. For example, the first stripes may be right-hand helices whereas the second stripes may be left-hand helices. This arrangement provides uniform bending properties in all directions. Although continuous stripes extending from adjacent the proximal end to adjacent the distal end normally are preferred, other patterns can be applied using the same process.

An electronic device may mounted inside the interior bore of the catheter, or disposed on or in the catheter wall. The electronic device may be connected to the ends of the stripes by techniques such as wire bonding (connection of the stripe to the device by a fine gold wire) or direct thermosonic bonding of the stripe end to the device. The portions of the stripes extending onto the hub at the proximal end of the catheter may be enlarged to form large, readily connectable pads on the hub.

The photoresist technique can be varied. For example the resist may harden only in unexposed areas, so that the exposed areas are removed, and the copper layer is removed in exposed areas but left in unexposed areas. In this case, the exposed areas will define gaps between the stripes. Also, the resist may be applied and patterned by exposure to light before the electroplating step, so that only those areas which do not bear resist will be electroplated.

Figure 4:
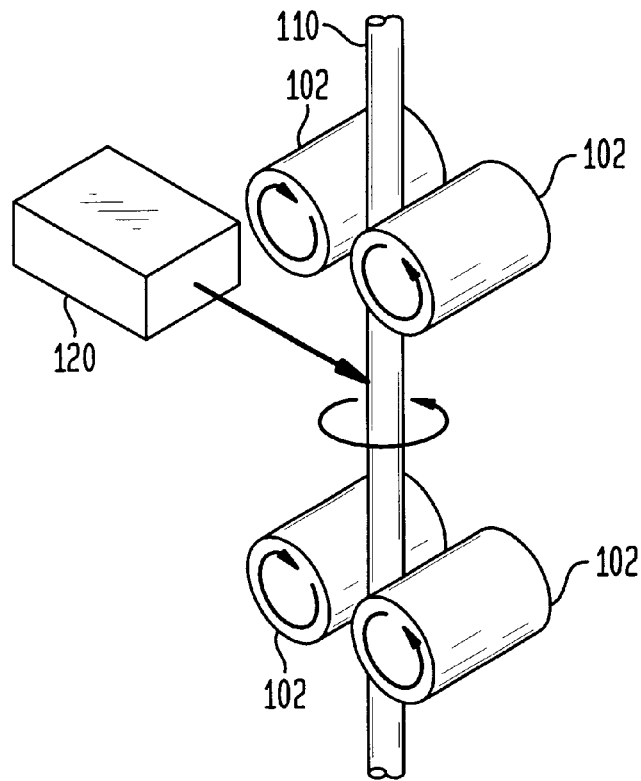
FIGS. 4 and 5 are views similar to FIG. 1 but depicting processes according to further embodiments of the invention.

As shown in FIG. 4, the same processes may be performed using continuous or semicontinuous tubes 110, by advancing the tube between rollers 102 while moving the light sources 120 (only one of which is shown) around the advancing tube. Here again, the width and pitch of each stripe can be varied along the length of the tube by changing the beam width and rate of rotation per unit advance as desired. Alternatively, the tube can be twisted as it advances, as by rotating one or both sets of rollers around the axis of the tube, as well as around the roller axes. The other steps, such as plating, etching and resist development, may be performed on a the tube as it is fed continuously through process chambers (not shown).

Figure 5:
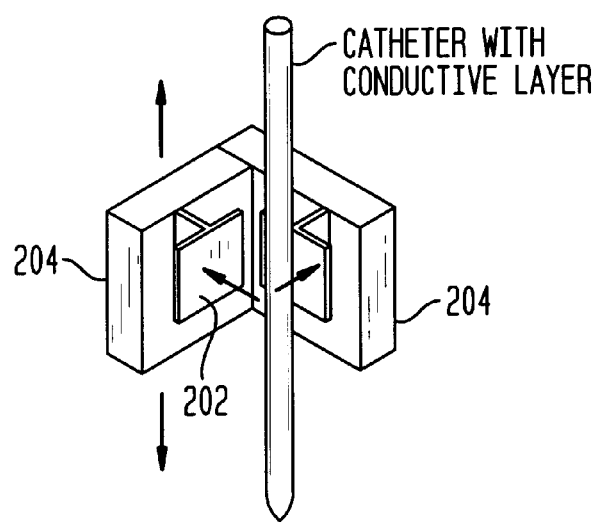

In a further embodiment, the catheter may be maintained stationary and the beam or beams of light may be moved lengthwise along the catheter while also rotating the beam or beams around the catheter, to achieve the same relative motion as discussed above. For example, the light source can include a movable light emitting element or a movable light-directing element such as a movable mirror or a fiber optic. This is advantageous where the catheter is of small diameter and substantial length, so that the catheter and supporting mandrel (if used) tend to flex laterally, i.e., transverse to the longitudinal axis. By holding the catheter in fixed position, flexing is minimized. The longitudinal axis of the catheter and mandrel extend vertically to further minimize flexing. In a further refinement, the actual position of the catheter may be sensed at numerous points along the length, so as to record a map of lateral flex versus length, and the motion of the light source may be compensated for lateral flex of the catheter. Thus, where the catheter is displaced in a particular lateral direction from its theoretical location, the light source can be similarly displaced. The actual position of the catheter can be detected by a conventional machine-vision system, provided that the light required by such system does not substantially expose photoresist. For example, if the photoresist is substantially sensitive only to ultraviolet light, the machine vision system may operate at infrared wavelengths. In another variant, the position of the catheter can be sensed by detecting capacitance or inductance between one or more probes of known position and the conductive layer on the catheter or a conductive mandrel within the catheter. For example, a pair of capacitive probes in the form of plates 202, and 203 as shown in FIG. 5, may be mounted to a carriage 204 which in turn is mounted for reciprocating motion on a track parallel to the theoretical longitudinal axis of the catheter. One plate 202 is offset from the theoretical axis in a first lateral direction, whereas the other plate 203 is offset from the axis in a second lateral direction orthogonal to the first lateral direction. Variation in capacitance between the conductive layer of the catheter and the first plate corresponds to variation in position in the first direction, whereas variation in capacitance between the catheter conductive layer and the second plate corresponds to variation in position in the second direction. In a further variation, a plurality of fixed capacitive or inductive probes may be disposed in an array around the catheter, and the position of the catheter can be deduced mathematically from the interaction between the catheter conductive layer (or mandrel) and all of these probes.

The terms "light" and "illuminating" as used herein should be understood as encompassing radiant energy outside of the visible spectrum as well as visible light. The radiant energy may be in the form of a beam or beams of charged particles, such as electron beams. Where charged particle beams are employed, the metallic layer on the tube desirably has a charge opposite to the charge of the particles. In this case, the beams will be attracted to the tube. If the tube is displaced from its theoretical position, the beams will tend to follow the tube. Accordingly, centering of the tube with respect to the beams may be less significant than with other forms of radiant energy. For example, the tube may be positively charged and the radiant energy may be in the form of electron beams. Also, the spiraling motion of the beams on the tube surface can include deflection of the electron beams imparted by controlled, varying magnetic or electrical fields to sweep the beams circumferentially around the tube. The focus of an electron beam can be varied to vary the strip width.

The word "catheter" as used in this disclosure should be understood as encompassing both the tubular devices commonly referred to as catheters and other tubular devices, such as those commonly referred to as endoscopes, endotracheal tubes, gastric tubes and others.

What is claimed is:

1. A method of making an elongated catheter comprising the steps of:

(a) providing a polymeric tube;
    (b) forming a metal on an exterior surface of the tube into a pattern including a plurality of elongated stripes of metal spaced circumferentially around said tube and extending lengthwise along the tube, said forming step including the steps of illuminating the exterior surface of the tube patternwise and treating said metal responsive to said illumination.

2. A method as claimed in claim 1 further comprising the steps of providing a polymeric layer over the outside of said tube and over said stripes.

3. A method as claimed in claim 2 further comprising the step of forming second metallic stripes over said polymeric layer, said second metallic stripes extending lengthwise along the tube.

4. A method as claimed in claim 3 wherein the steps of forming said first and second stripes are performed so that said first stripes are helical and have a first pitch direction, and so that said second stripes are helical and have a second pitch direction opposite to said first pitch direction.

5. A method of making an elongated catheter comprising the steps of:

(a) providing a polymeric tube;

(b) forming a metal on an exterior surface of the tube into a pattern including a plurality of elongated stripes of metal spaced circumferentially around said tube and extend lengthwise along the tube, said forming step including the steps of illuminating the exterior surface of the tube patternwise and treating said metal responsive to said illumination, said forming step further including the steps of providing a layer of said metal on said exterior surface and a layer of a resist on said metal layer before said illuminating step so that said resist is selectively developed responsive to said illumination to leave elongated stripes of resist corresponding to said stripes of metal overlying said layer with gaps therebetween, and then exposing the exterior surface of the tube to an etchant to remove the metal in said gaps.

6. A method of making an elongated catheter comprising the steps of:

(a) providing a polymeric tube;

(b) forming a metal on an exterior surface of the tube into a pattern including, a plurality of elongated stripes of metal spaced circumferentially around said tube and extending lengthwise along the tube, said forming step including the steps of illuminating the exterior surface of the tube patternwise and treating said metal responsive to said illumination, said forming step further including the steps of providing a resist on said exterior surface of said tube prior to said illuminating step so that said resist is selectively developed responsive to said illumination to leave a layer of resist with elongated gaps corresponding to said stripes of metal overlying said exterior surface and then depositing said metal on said exterior surface so that said metal adheres to said exterior surface only in said gaps.

7. A method of making an elongated catheter comprising the steps of:

(a) providing a polymeric tube;

(b) forming a metal on an exterior surface of the tube into a pattern including a plurality of elongated stripes of metal spaced circumferentially around said tube and extending lengthwise along the tube, said forming step including the steps of illuminating the exterior surface of the tube patternwise and treating said metal responsive to said illumination, said illuminating step including the steps of advancing said tube lengthwise through a plurality of light beams transverse to the tube so that said light beams impinge on the tube and trace exposed stripes along the length of the tube.

8. A method as claimed in claim 7 wherein said step of exposing said resist to light further includes the step of rotating said light beams and said tube relative to one another so that said light beams trace said exposed stripes helically along the length of the tube.

9. A method as claimed in claim 8 wherein said rotating step and said advancing step are performed so as to vary the amount of rotation per unit length of advance along the length of the tube and thereby form said helical exposed stripes with varying pitch along the length of the tube.

10. A method as claimed in claim 8 further comprising the step of providing an additional polymeric layer overlying said metallic stripes on the exterior surface of said tube and repeating said forming step to provide additional metallic stripes overlying said additional polymeric layer.

11. A method as claimed in claim 10 wherein said step of repeating said forming step includes said advancing and rotating steps with the direction of said rotation is reversed relative to the direction of advancement.

12. A method as claimed in claim 4 further comprising the step of varying the cross-sectional areas of said light beams where said light beams impinge on the tube to thereby vary the width of the exposed stripes along the length of the tube.

\* \* \* \* \*